US010842164B2

(12) United States Patent
Priemer et al.

(10) Patent No.: US 10,842,164 B2
(45) Date of Patent: Nov. 24, 2020

(54) COMPOSITION CONTAINING AMINO ACIDS AND PROCESS FOR PRODUCING SAME

(71) Applicants: Wolfgang Priemer, Buende (DE); Robert Finke, Fuebbecke (DE)

(72) Inventors: Wolfgang Priemer, Buende (DE); Robert Finke, Fuebbecke (DE)

(73) Assignee: Wolfgang Priemer, Buende (DE)

( * ) Notice: Subject to any disclaimer, the term of this patent is extended or adjusted under 35 U.S.C. 154(b) by 148 days.

(21) Appl. No.: 16/070,037

(22) PCT Filed: Jan. 13, 2017

(86) PCT No.: PCT/EP2017/050683
§ 371 (c)(1),
(2) Date: Jul. 13, 2018

(87) PCT Pub. No.: WO2017/121859
PCT Pub. Date: Jul. 20, 2017

(65) Prior Publication Data
US 2019/0029280 A1    Jan. 31, 2019

(30) Foreign Application Priority Data

Jan. 13, 2016  (DE) .................. 10 2016 000 286
Jan. 13, 2016  (DE) .................. 20 2016 000 228 U

(51) Int. Cl.
| | | |
|---|---|---|
| A23C 9/12 | (2006.01) |
| A61K 8/64 | (2006.01) |
| A61K 8/44 | (2006.01) |
| A61K 8/49 | (2006.01) |
| A61Q 19/10 | (2006.01) |
| A61Q 5/00 | (2006.01) |
| A61Q 5/12 | (2006.01) |
| A61Q 19/00 | (2006.01) |
| A61K 8/896 | (2006.01) |
| C11D 9/40 | (2006.01) |
| C11D 3/38 | (2006.01) |

(52) U.S. Cl.
CPC .............. *A23C 9/1209* (2013.01); *A61K 8/44* (2013.01); *A61K 8/492* (2013.01); *A61K 8/64* (2013.01); *A61K 8/896* (2013.01); *A61Q 5/002* (2013.01); *A61Q 5/12* (2013.01); *A61Q 19/00* (2013.01); *A61Q 19/10* (2013.01); *C11D 3/38* (2013.01); *C11D 9/40* (2013.01); *A23V 2002/00* (2013.01); *A23V 2250/063* (2013.01); *A23V 2250/065* (2013.01); *A23V 2250/0626* (2013.01); *A23V 2250/0632* (2013.01); *A23V 2250/0638* (2013.01); *A23V 2250/0648* (2013.01); *A23V 2250/0654* (2013.01); *A23V 2250/1578* (2013.01); *A23V 2250/161* (2013.01); *A23V 2250/54252* (2013.01); *A23V 2250/55* (2013.01); *A61K 2800/805* (2013.01)

(58) Field of Classification Search
CPC ........ A23C 9/1209; A61K 8/44; A61K 8/492; A61K 8/64; A61K 8/896; A61K 2800/805; A61Q 5/002; A61Q 5/12; A61Q 19/00; A61Q 19/10; C11D 9/40; A23V 2002/00; A23V 2250/0626; A23V 2250/063; A23V 2250/0632; A23V 2250/0638; A23V 2250/0648; A23V 2250/065; A23V 2250/0654; A23V 2250/1578; A23V 2250/161; A23V 2250/54252; A23V 2250/55

See application file for complete search history.

(56) References Cited

U.S. PATENT DOCUMENTS

| | | | |
|---|---|---|---|
| 4,358,465 A | 11/1982 | Brule et al. | |
| 6,413,561 B1* | 7/2002 | Sass ............... | A23C 9/1322 426/590 |
| 2004/0161493 A1* | 8/2004 | Souppe ........... | A21D 2/263 426/41 |

FOREIGN PATENT DOCUMENTS

| | | |
|---|---|---|
| CA | 1112173 | * 11/1981 |
| CN | 104664375 | 6/2015 |
| DE | 102015002418 | 8/2016 |
| EP | 0457565 | 11/1991 |
| EP | 1008303 | * 12/1999 |
| GB | 1308690 | 2/1973 |
| JP | H02-234642 | 9/1990 |
| JP | H06-165655 | 6/1994 |
| WO | WO 2014/130007 | 8/2014 |

OTHER PUBLICATIONS

Dipeptidyl-peptidases. Handbook of Proteolytic Enzymes. vol. 3. 2013. p. 3392.*
Subtilisin. Wikipedia. 2020. https://en.wikipedia.org/wiki/Subtilisin.*
Why Purify Enzymes. Kornberg. Methods in Enzymology. vol. 463. 2009. pp. 3-6.*
Enzyme Technology. 2014. http://www1.lsbu.ac.uk/water/enztech/sources.html.*
Calcium Carbonate in Foods. 2012. https://web.archive.org/web/20150930234013/https://www.livestrong.com/article/555678-calcium-carbonate-in-foods-milk-allergies/.*

(Continued)

*Primary Examiner* — Anthony J Weier
(74) *Attorney, Agent, or Firm* — Sheridan Ross, P.C.

(57) ABSTRACT

The invention relates to a process for the preparation of a composition including free amino acids, oligopeptides and polypeptides, characterized in that the process comprises at least the following step: adding at least two different peptidases, which are present in purified form, to a composition comprising at least one protein.

23 Claims, No Drawings

(56) References Cited

OTHER PUBLICATIONS

International Search Report prepared by the European Patent Office dated Mar. 2, 2017, for International Application No. PCT/EP2017/050683.

* cited by examiner

COMPOSITION CONTAINING AMINO ACIDS AND PROCESS FOR PRODUCING SAME

CROSS REFERENCE TO RELATED APPLICATIONS

This application is a national stage application under 35 U.S.C. 371 and claims the benefit of PCT Application No. PCT/EP2017/050683 having an international filing date of 13 Jan. 2017, which designated the United States, which PCT application claimed the benefit of German Patent Application No. 10 2016 000 286.7 filed 13 Jan. 2016, and German Patent Application No. 20 2016 000 228.8 filed 13 Jan. 2016, the disclosure of each of which are incorporated herein by reference.

The present invention relates to a composition comprising free amino acids, oligopeptides, and polypeptides, as well as to the production of the same by enzymatic digestion of natural protein sources. The invention is described particularly in the context of the use in food/beverage production, in cosmetics and soap production, or in the production of personal care and slimming products. It should be pointed out that the invention is also applicable to other areas, for example the production of animal food.

The 20 proteinogenic amino acids are the building blocks of all cellular proteins, including structural proteins, transport proteins, storage proteins, immunoglobins, and enzymes. Most higher organisms depend on food to supply them with individual amino acids (essential amino acids). In humans, these are isoleucine, leucine, lysine, methionine, phenylalanine, threonine, tryptophan, and valine. A sufficient supply of amino acids is essential for protein synthesis. Protein synthesis is thus limited quantitatively by the individual limiting amino acid. Protein synthesis is indispensable for all cellular processes. An inadequate supply of amino acids leads to deficiency diseases, marasmus, and a significant weakening of the immune system, and it has impacts on the vitality and outer appearance of hair, nails, and skin. An adequate supply of amino acids is therefore particularly important for people who play sports, and also for people who wish to lose weight or people with poor food assimilation/food utilization due to existing health problems, but who wish to be quickly and fully supplied with amino acids and peptides/proteins for maintaining resistance and musculature or for increasing muscle development.

Amino acids are also constituents of NMF (natural moisturizing factor), a main component of the skin responsible for moisture regulation and other skin functions, and collagen, one of the most important structural proteins of connective tissue and skin. Free amino acids also stabilize the protective acid mantle of the skin. For these reasons, amino acids, peptides, and proteins are used in skin and hair cosmetics.

Amino are acids are ingested with food, mainly in the form of proteins that are then hydrolyzed in the stomach and the small intestine. The resulting amino acids, as well as di- and tripeptides, are reabsorbed in the intestine. It is known that bioavailability can be accelerated significantly by ingestion of already pre-digested, i.e., hydrolyzed, proteins. Free amino acids can virtually be reabsorbed immediately once they reach the intestine. Sports physicians in particular administer amino acids after training and point out that it takes about 30 minutes for the amino acids to be absorbed in the bloodstream. By comparison, consuming eggs would not lead to amino acid absorption until more than five hours later. In the meantime, supply gaps may occur and the immune system may be weakened.

DE 196 06 439 A describes a process for the enzymatic degradation of proteins. In the process described therein, preferably protease-producing microorganisms are used rather than purified proteases, which are generated and provided separately.

The invention is based on the object of providing an alternative process for producing a composition comprising free amino acids, oligopeptides, and polypeptides.

This is achieved according to the invention by the teaching of independent claim 1. Preferred embodiments of the invention are the subject matter of the dependent claims.

According to a first aspect, the invention relates to a process for producing a composition comprising free amino acids, oligopeptides, and polypeptides.

A process according to the invention comprises at least the step of adding at least two different peptidases, which are present in purified form, to a composition that comprises at least one protein.

In the context of the present invention, it was found that with appropriate design, the yield of free amino acids and/or of oligopeptides with a length of up to 10 amino acids in the enzymatic digestion of at least one protein can be improved if instead of adding peptide-producing bacteria, at least two peptidases in purified form are added to the at least one protein. In particular, it was found that with appropriate design of the production process, compositions with all eight amino acids essential for humans or even with all twenty proteinogenic amino acids can be obtained by using two different purified peptidases. Compositions generated by the production process according to the invention are therefore suitable for filling supply gaps of individual amino acids and can thus prevent deficiency diseases or deficiency symptoms such as those of the skin or hair, marasmus, and weakening of the immune system.

The composition can optionally also comprise varying quantities of the uncleaved source protein, depending upon the duration and efficiency of the fermentation and the quantity of peptidases used.

It was furthermore found that, the process duration of the process according to the invention with appropriate design can be shortened in comparison to the bacterial fermentation of proteins, i.e., the enzymatic digestion of proteins by adding peptidase-producing bacteria. The production cycles can thus be designed more efficiently and the use of large fermentation tanks becomes unnecessary.

Amino acid-containing compositions that are obtained by conventional bacterial fermentation, i.e., by adding peptidase-producing bacteria, typically have a distinct bitter taste. In addition, a strong foul taste is frequently reported, which can render such compositions virtually unsuitable for human consumption. Surprisingly, both foul and bitter tastes can be reduced or even completely eliminated by the process according to the invention with appropriate design. The amino acid-containing compositions produced by the process according to the invention can, with appropriate design of the process, be free of off-flavors and free of cheesy aftertastes.

In the context of the invention, the term 'protein' is understood to mean organic molecules that are composed of amino acids interconnected by peptide bonds. Proteins in the context of the invention are undigested, in other words not originating from hydrolysis of a larger protein. In the context of the invention, the size of proteins is not limited, although preferably proteins comprise at least 100 amino acids. Proteins in the context of the invention comprise in particular animal, vegetable, and fungal proteins, although the use of proteins of bacterial or other microbial origin as a starting substrate for enzymatic hydrolysis is not excluded. Proteins in the context of the invention are not in any way limited in terms of their secondary, tertiary, and quaternary structure and include globular and fibrillary proteins. Nor are proteins in the context of the invention limited in terms of their function, and therefore include structural proteins, transport proteins, storage proteins, immunoglobulins, enzymes, and others.

The term 'peptidase' in the context of the invention is understood to mean enzymes capable of cleaving proteins or peptides. Peptidases catalyze the hydrolysis of peptide bonds in peptides and proteins. The terms 'protein or peptide cleavage', 'protein or peptide digestion', and 'hydrolysis of peptide bonds' are used synonymously here. The term 'fermentation of proteins, peptides, or protein sources' in the context of the invention is understood to mean the enzymatic cleavage of proteins and peptides. The term 'bacterial fermentation' is understood to mean fermentation by adding peptidase-producing bacteria. The term 'enzymatic fermentation' is understood to mean fermentation by adding purified peptidases. The term 'peptidase' is used synonymously with the terms 'protease' and 'proteinase' here. In the context of the invention, the term 'peptidase' is understood to mean the enzyme in purified form, unless expressly mentioned otherwise. The term 'in purified form' is understood to mean the presence of the enzyme in free form in an enzyme preparation. Such enzyme preparations can be produced in any manner, for example by isolation and purification of the enzyme after homologous or heterologous expression in microorganisms. The use of purified peptidases offers the advantage over the use of peptidase-producing bacteria of better controllability and reproducibility of the process. Furthermore, the risk of contamination with bacteriophages can be avoided.

In the context of this invention, the term 'free amino acids' is understood to mean amino acids that do not have peptide bonds to other amino acids. Free amino acids in the context of the invention arise through the enzymatic digestion of proteins or peptides, including oligopeptides, through the enzymatic hydrolysis of peptide bonds in these proteins or peptides.

The term 'peptide' in the context of the invention is understood to mean a cleavage product of a protein that arises through enzymatic hydrolysis of one or two of the peptide bonds in the protein.

The term 'oligopeptide' in the context of the invention is understood to mean a peptide, i.e., a cleavage product of a protein produced by enzymatic digestion, which consists of 2 to 10 amino acids. The term oligopeptide therefore encompasses the terms dipeptide (peptide consisting of two amino acids), tripeptide (peptide consisting of three amino acids), tetrapeptide (peptide consisting of four amino acids), and pentapeptide (peptide consisting of five amino acids).

The term 'polypeptide' in the context of the invention is understood to mean a peptide, i.e., a cleavage product of a protein produced by enzymatic digestion, which consists of at least 11 amino acids. The only restriction on the upper limit of the length of a polypeptide in the context of the invention is that the polypeptide must have at least one fewer amino acid than the source protein, the cleavage of which gave rise to the polypeptide.

Compositions that are generated by the production process according to the invention have the advantage over standard dietary protein that amino acids and oligopeptides can be reabsorbed significantly faster in the body than can uncleaved proteins. Free amino acids are reabsorbed virtually immediately upon reaching the small intestine. Depending upon the quantity of the amino acids consumed, reabsorption may last for example as long as an hour. Oligopeptides must be cleaved into free amino acids before they can be reabsorbed, thus delaying reabsorption by approximately half an hour. In the case of polypeptides, cleavage into free amino acids in the small intestine takes about one to two hours, depending upon the length of the polypeptide. The production process according to the invention thus provides compositions that ensure a rapid, almost immediate, progressive supply of amino acids. A continuous supply of amino acids of virtually immediate onset and several hours in duration is enabled by the simultaneous presence of free amino acids, short oligopeptides, longer polypeptides, and optionally still uncleaved proteins in the composition.

In personal care products, the amino acids and oligopeptides generated by the process according to the invention can serve as a protein source for the formation of collagen and elastin, which occur naturally in the skin. Collagens possess a high molecular weight and are therefore unable to penetrate the skin. They have a skin toning effect and are highly moisture binding. Soluble collagen accelerates wound healing and spontaneous re-epithelization of the skin. In doing so, it stimulates tissue reconstruction and macromolecule formation.

Peptides are also part of the connective tissue, hair and nails. They act as messenger substances, hormones, or coenzymes and play key roles in nearly all biological processes. They thus accelerate healing processes and cell renewal. Peptides often have regulatory functions. For example, insulin is a peptide that controls sugar metabolism in the body.

Peptides, in particular oligopeptides, are partially broken down on the skin surface into free amino acids and thus enhance the natural moisture content of the skin. As constituents of NMF (natural moisturizing factor), amino acids play an important role in moisture regulation and other functions of the skin. Furthermore, free amino acids stabilize the acid mantle of the skin.

Preferred embodiments of the invention are described in the following.

According to a preferred embodiment, at least one exopeptidase and at least one endopeptidase are added to the composition comprising at least one protein. This embodiment has the advantage over the exclusive use of endo- or exopeptidases that, for the same total amount of peptidases used and for the same process duration, the content of free amino acids and/or of oligopeptides can be increased at the expense of the polypeptides and/or of the at least one source protein, in other words of the at least one protein in the composition comprising at least one protein. Specifically, this embodiment has the advantage that with appropriate design, an ideal proportion of free amino acids, oligopeptides, and polypeptides is achievable.

In the context of the invention, the term 'endopeptidase' is understood to mean a peptidase that is capable of catalyzing the hydrolytic cleavage of peptide bonds within a peptide chain. The cleavage products each have at least two amino acids, typically more amino acids.

In the context of the invention, the term 'exopeptidase' is understood to mean a peptidase that is capable of catalyzing the cleavage of individual amino acids at the ends of a peptide chain.

An ideal composition is characterized by a high content of free amino acids and oligopeptides. Preferably 0.5 to 25 wt % free amino acids, 10 to 80 wt % oligopeptides, and at most 40 wt % uncleaved source protein, based on the total weight of free amino acids, oligopeptides, polypeptides, and proteins without the added peptidases, are contained in the composition generated by the production process. More preferably 2 to 20 wt % free amino acids, 25 to 65 wt % oligopeptides, and at most 10 wt % uncleaved source protein, based on the total weight of free amino acids, oligopeptides, polypeptides, and proteins without the added peptidases, are contained in the composition generated by the production process. By comparison, in conventional fermentation of protein sources by peptide-producing bacteria, depending upon the duration of fermentation, which is typically a few days up to several weeks or even years, as for example in the traditional KOSO-process from Japan, only about 1 to at most 12 wt % free amino acids based on the total weight of free amino acids, oligopeptides, polypeptides, and proteins are obtained.

The content of free amino acids and oligopeptides in the composition produced is determined by the method described in the following. After incubation with the at least two peptidases is complete, samples are taken and homogenized. 0.5 g-2.5 g of the homogenized sample are weighed to the nearest 0.1 mg into a Falcon tube. 1 ml norleucine solution (0.1312 g/200 ml) are added as an internal standard (IS) and topped up to 25 ml with 3% 5-sulfosalicylic acid. The tubes are placed in a shaker and shaken vigorously for 20 minutes. They are then centrifuged for 5 minutes at 5000 rpm. The supernatant is filtered through a syringe filter (0.45 μm). 0.5 ml of the filtrate and 0.5 ml sample buffer for chromatography are pipetted into a reaction vessel, which is then sealed. The solution thus produced is used for chromatographic analysis on an amino acid analyzer.

The amino acid composition of the fraction containing free amino acids and oligopeptides (water-soluble NPN fraction of the composition) is determined in conjunction herewith. To this end, 0.5 g-2.5 g of the homogenized sample are again weighed to the nearest 0.1 mg into a Falcon tube. 2.5 ml norleucine solution as an internal standard (IS) are pipetted in and topped up to 25 ml with 3% 5-sulfosalicylic acid. The tubes are shaken and centrifuged as described above; the water-insoluble peptides and proteins contained in the precipitate are discarded. 1 ml of the supernatant is pipetted into a 50 ml glass digestion vessel, mixed with 9 ml 6N hydrochloric acid, and the vessels are tightly sealed with a screw cap. The vessels are set in a heating block and the sample solution is digested for 8 h at 105° C. 2 ml of the digested solution are evaporated to dryness. The residue is taken up in 1 ml sample buffer for chromatography and transferred to a reaction vessel, which is sealed. The solution thus produced is used for chromatographic analysis on an amino acid analyzer. In addition, the content of oligopeptides in the composition can be calculated by subtracting the content of free amino acids determined in step 1.

Preferably about 40 to 80 wt %, more preferably about 50 to 70 wt %, of the free amino acids are essential amino acids, namely isoleucine, leucine, lysine, methionine, phenylalanine, threonine, tryptophan, and valine.

Preferably all 20 proteinogenic amino acids, namely the amino acids isoleucine, leucine, lysine, methionine, phenylalanine, threonine, tryptophan, valine, alanine, arginine, aspartic acid, asparagine, cysteine, glutamine, glutamic acid, glycine, histidine, proline, serine, and tyrosine, are contained in the composition generated by the production process according to the invention.

The simultaneous presence of free amino acids, oligopeptides, and polypeptides in said concentrations and in the resulting ratios to each other in the produced composition offers the advantage of a progressive, continuous supply of amino acids with basically immediate onset after ingestion of the composition over several hours.

According to a preferred embodiment, the at least two different peptidases are of microbial origin, preferably of bacterial or fungal origin. Microbial peptidases are considerably more diverse in comparison to human or mammalian peptidases. This embodiment has the advantage that protein sources not readily metabolizable by human beings can also be efficiently digested.

The term 'of microbial origin' is understood to mean peptidases with amino acid sequences corresponding to those of microbial peptidases, in other words to peptidases expressed endogenously in microorganisms. In the context of the invention, the organism in which the peptidase is produced (for example by heterologous expression) is irrelevant to the designation. Peptidases of microbial origin are thus expressed endogenously in microorganisms. In the context of the invention, microorganisms are understood to mean the totality of all organisms that cannot be discerned with the naked eye. This includes viruses, bacteria, archaea, protozoa, fungi, and microalgae.

According to a preferred embodiment, the composition comprising at least one protein has a protein concentration of 1 to 40 wt %, preferably 5 to 30 wt %, more preferably 10 to 20 wt %, based on the total weight of the composition comprising at least one protein. It was found that the aforementioned substrate concentrations are advantageous for enzyme activity, because the enzyme and the substrate can come in contact comparatively fast. This embodiment thus offers the advantage of good yields of free amino acids and/or oligopeptides and/or a short process duration.

According to a preferred embodiment, the composition comprising at least one protein is incubated with at least one of the at least two different peptidases for at least 1 h, preferably for a period of 1 h to 24 h, more preferably for a period of 4 h to 12 h, most preferably for a period of 6 h to 10 h. The advantage of this embodiment is that both the demand for an efficient cleavage of the at least one source protein and the demand for a time-efficient process are fulfilled. An ideal proportion of free amino acids, oligopeptides, and polypeptides can be obtained with the aforementioned incubation times.

According to a preferred embodiment, the composition comprising at least one protein is incubated with at least two different peptidases at a temperature of at least 37° C., preferably at a temperature of 40° C. to 60° C., more preferably at a temperature of 45° C. to 55° C. The advantage of this embodiment is that a contamination with bacteria and consequently a contamination with bacteriophages can be avoided by these relatively high temperatures. Health risks are thus minimized and decay processes, which can negatively impact the taste and odor of the final product, are thus prevented. Because enzyme producers typically recommend incubation temperatures of about 37° C. for peptidases in order to prevent enzyme denaturation at higher temperatures, the finding that an enzymatic hydrolysis of proteins is feasible at such relatively high temperatures was completely surprising. It was found that at temperatures of about 50° C., the peptides used exhibit particularly high activities and that the production process can thus be shortened. To obtain optimum yields of free amino acids and oligopeptides, it can be useful to use the at least two peptidases in higher quantities than normally recommended for enzymatic digestion at 37° C. In addition, repeated addition of the peptidases during the production process can have positive effects on the yield of free amino acids and oligopeptides.

According to a preferred embodiment, at addition of the at least two different peptidases the composition comprising at least one protein has a pH of 3 to 7, preferably of 4 to 6, more preferably of 4.5 to 5.5, wherein optionally the pH is adjusted by adding at least one organic acid, in particular selected from lactic acid, citric acid, and malic acid and/or by adding lactic acid bacteria. Preference is given to not adding any bacteria or other microorganisms, for example yeasts, during the production process. The aforementioned pH ranges are optimal for the enzyme activity of peptidases. In the case of conventional fermentation with peptidase-producing bacteria on the other hand, the pH must be lowered to about 3 to 4. The generated fermented product has a very sour taste as a result. By using purified peptidases in a pH range of greater than 4, the taste of the generated product can be significantly improved. The generated compositions have a slightly acidic to neutral taste.

According to a preferred embodiment, the process also comprises the step of adding calcium carbonate and/or magnesium carbonate, wherein preferably the addition takes place after addition of the at least two different peptidases, more preferably after the end of the incubation of the composition comprising at least one protein with the at least two peptidases. The advantage of this embodiment is that the ratio of calcium to magnesium in the final product can be adjusted to a desired value. The weight ratio of magnesium to calcium in the generated composition is preferably about 1.25:1 to about 3:1, more preferably about 1.5:1 to about 2.5:1, and most preferably about 2:1. An additional advantage of this embodiment is that the pH of the final product can be raised after enzymatic hydrolysis is complete, thus making it possible to improve the taste of the final product.

According to a preferred embodiment, the composition comprising at least one protein comprises at least one protein source selected from whey, whey protein concentrate, milk protein concentrate, slurry from food production such as distillery slurry or brewery slurry, peas, lentils, beans, soybeans, and a combination of two or more thereof. The use of natural protein sources such as the ones mentioned above has the advantage that the naturally occurring ingredients in these protein sources such as coenzymes, vitamins, and trace elements are maintained in the generated composition and can effect a particularly rapid and/or efficient reabsorption in the intestine. In principle, all types of protein sources are conceivable as substrates for the production process according to the invention. Depending upon the use of the final product, particularly high-quality protein sources such as whey and milk protein concentrate, vegetable protein sources such as soybean, peas, lentils, beans, brewery and distillery slurries for producing vegetarian or vegan products, or relatively inexpensive protein sources such as brewery and distillery slurries can be selected and optionally combined. In addition to the high value, whey as a protein source also has the advantage of a high content of additional ingredients of value to human beings such as vitamins, coenzymes, minerals, and others. This 'whey matrix' also increases the bioavailability of amino acids, oligopeptides, and polypeptides by accelerating reabsorption. Supplying amino acids and oligopeptides that are present in such a whey matrix is deemed more efficient than supplying chemically synthesized amino acids, which are added to a product.

Whey protein concentrate has the additional advantage of a high protein content of about 80% and a low carbohydrate and fat content. Whey protein concentrate is thus comparatively low in calories. Furthermore, it has a very low lactose content. Regardless of the protein source used, the lactose remaining in the final product can optionally be removed without any problem, for example by adding purified lactase or lactase-producing *lactobacilli*.

In the context of the invention, the term 'protein source' is understood to mean a composition comprising at least one protein, preferably a protein mixture. The term 'Protein' as used in this context encompass animal, vegetable, and microbial proteins.

According to a preferred embodiment, the total amount of added peptidase is each from 500 to 20,000, preferably from 1000 to 15,000, more preferably from 2000 to 10,000 U per 100 grams of the at least one protein in the composition comprising at least one protein.

In the context of the invention, a U is understood to mean the quantity of enzyme that cleaves one micromole of substrate protein per minute at 37° C.

According to another preferred embodiment, the total amount of added peptidase is each from 0.5 to 20, preferably from 1 to 15, more preferably from 2 to 10 grams per 100 grams of the at least one protein in the composition comprising at least one protein.

The provided amounts of added peptidase are higher than the manufacturers' recommendations for an enzymatic digestion at 37° C. These embodiments have the advantage that the efficiency of the enzymatic digestion of the at least one source protein can be increased, and that consequently the yield of free amino acids and/or oligopeptides can be increased and/or that the duration of the production process can be decreased. It was surprisingly found that the use of peptidases in excess, for example in the provided quantity ranges, permits an increase of the incubation temperature to over 40° C. up to about 60° C., without enzymatic hydrolysis coming prematurely to a standstill as a result of enzyme degradation. Increasing the incubation temperature to over 40° C. in turn reduces or completely prevents the risk of contamination with bacteria, including bacterial pathogens, thus simultaneously reducing or completely preventing the risk of contamination with bacteriophages. The production process is preferably carried out at about 45° C. to about 55° C., more preferably at about 50° C., because in this temperature range a contamination with bacteria and/or bacteriophages can be prevented and at the same time the degradation of the added peptidases can be minimized.

According to a preferred embodiment, at least one of the at least two peptidases is added repeatedly to the composition comprising at least one protein. The advantage of this embodiment is that the premature standstill of the process due to degradation of the added peptidases can be prevented, or more specifically that the total quantity of added peptidase can be reduced, in particular at incubation temperatures of over 40° C., over 45° C., or at about 50° C.

According to a preferred embodiment, at least one of the at least two peptidases is added repeatedly in essentially equal amounts and in essentially equal time intervals to the composition comprising at least one protein. By adding the peptidases repeatedly in essentially equal amounts and in essentially equal time intervals, it was found that the efficiency of the enzymatic hydrolysis can be increased, or that given comparable composition of the final product obtained, the total quantity of peptidases used can be reduced.

According to a preferred embodiment, the at least one endopeptidase is added before adding the at least one exopeptidase. Surprisingly, it was found that by doing so the bitter taste of the generated composition can be reduced or even entirely eliminated. In particular, the amino acids valine, leucine, isoleucine, and arginine have a bitter taste. A high concentration of these free amino acids can render a composition very bitter to inedible. Amino acid-containing compositions that are obtained by bacterial fermentation, in other words by adding peptidase-producing bacteria, typically have a distinct bitter taste, which can make them unsuitable for human consumption. The reduced bitterness of the composition generated by the process according to the invention could be a result of the formation of ornithine during enzymatic digestion. It is known that ornithine can help reduce the bitterness of amino acid-containing compositions.

According to a preferred embodiment, the composition comprising at least one protein is initially incubated with the at least one endopeptidase for 1 to 10 h, preferably for 2 to 6 hours, more preferably for about 5 h, and then incubated with the at least one exopeptidase for 3 to 40 h, preferably for 20 to 40 h, more preferably for about 30 h; the incubation with the exopeptidase is preferably in the presence of the at least one endopeptidase. The at least one endopeptidase and/or the at least one exopeptidase are/is preferably added repeatedly, preferably twice, three times, four times, five times, or six times, in essentially equal amounts and in essentially equal time intervals. The advantage of this embodiment is that a composition with optimum proportions of free amino acids, oligopeptides, and polypeptides is obtained.

According to a second aspect, the invention relates to a composition comprising free amino acids, oligopeptides, and polypeptides that can be obtained by at least one of the process described herein.

According to a third aspect, the invention relates to a composition comprising free amino acids, oligopeptides, polypeptides, coenzymes, vitamins, and trace elements, with preference given to said composition comprising at least the following free amino acids: isoleucine, leucine, lysine, methionine, phenylalanine, threonine, tryptophan, and valine; wherein more preferably said composition comprises the 20 proteinogenic amino acids isoleucine, leucine, lysine, methionine, phenylalanine, threonine, tryptophan, valine, alanine, arginine, aspartic acid, asparagine, cysteine, glutamine, glutamic acid, glycine, histidine, proline, serine, and tyrosine.

According to a preferred embodiment, the free amino acids, oligopeptides, and polypeptides were obtained by enzymatic hydrolysis of at least one protein with at least two different purified peptidases. This embodiment offers the advantage over standard fermentation of protein sources by peptidase-producing bacteria or other microorganisms of particularly high contents of free amino acids and/or oligopeptides in the composition. In particular with appropriate design of the enzymatic hydrolysis with the at least two different purified peptidases, it is possible to obtain a composition with all eight amino acids essential for human beings or even with all twenty proteinogenic amino acids. These compositions are thus suitable for filling supply gaps in individual amino acids and can thus prevent deficiency diseases, marasmus, and weakening of the immune system.

According to a preferred embodiment, the composition comprises from 0.5 wt % to 25 wt %, preferably 2 wt % to 20 wt %, more preferably 5 wt % to 15 wt % free amino acids, based on the total weight of free amino acids, oligopeptides, polypeptides, and proteins without the added peptidases.

According to another preferred embodiment, the composition comprises from 0.3 to 15 wt %, preferably 1.2 wt % to 12 wt %, more preferably 3 to 9 wt % in total of the free essential amino acids isoleucine, leucine, lysine, methionine, phenylalanine, threonine, tryptophan, and valine, based on the total weight of free amino acids, oligopeptides, polypeptides, and proteins without the added peptidases.

According to another preferred embodiment, the composition comprises from 10 to 80 wt %, preferably 25 to 65 wt % oligopeptides, based on the total weight of free amino acids, oligopeptides, polypeptides, and proteins without the added peptidases.

According to another preferred embodiment, 0 wt % to 40 wt %, preferably 0 wt % to 20 wt %, more preferably 0 wt % to 10 wt % of the at least one source protein for the enzymatic hydrolysis are present in the composition as uncleaved protein.

These embodiments have the advantage of progressive, continuous supply of amino acids with basically immediate onset after ingestion of the composition for several hours.

According to another preferred embodiment, the composition has a pH of 3 to 7, preferably of 4 to 6, more preferably of 4.5 to 5.5. This embodiment has the advantage that the pH of the composition is similar to that of the skin and can therefore be advantageously used for the production of personal care products. This embodiment also has the advantage that it is relatively neutral in taste, in particular not too sour, and can therefore be advantageously used for the production of food products.

According to a preferred embodiment, the weight ratio of magnesium to calcium in the composition is from 1.25:1 to 3:1, preferably 1.5:1 to 2.5:1, more preferably about 2:1.

The composition can be used directly after enzymatic digestion, without any further purification and/or isolation steps, for the production of food products or personal care products. The elimination of individual components from the composition, such as lactose or uncleaved protein and/or water-insoluble polypeptides, for example, is also conceivable. The volume of the composition obtained by enzymatic digestion can also be reduced by any method, or a powder comprising amino acids and oligopeptides as well as optionally polypeptides and/or uncleaved protein can be prepared from the generated composition.

According to a fourth aspect, the invention relates to the use of the composition according to the invention for producing a food product, in particular for producing a fruit juice beverage, a milk beverage, a whey beverage, a yogurt, an ayran, or a kefir.

According to a preferred embodiment, a portion of the water of a food product, in particular of a known food product, is replaced with the composition according to the invention. Food products can thus be particularly easily 'refined' and improved in value by adding the composition according to the invention.

According to a fifth aspect, the invention relates to the use of the composition according to the invention for producing a personal care product, in particular for producing a soap, a shampoo, a hair treatment, a hair mask, a hair pack, a hair tonic, a conditioner, a bath essence, a body lotion, a body gel, a lotion for treating rosacea, a cream for treating acne, a facial mask or a facial cream.

According to a preferred embodiment, a portion of the water, preferably at least 80% of the water, of a personal care product, in particular of a known personal care product, preferably of a soap, is replaced with the composition according to the invention. Personal care products can thus be particularly easily 'refined' and improved in value by adding the composition according to the invention. In particular, the improved skin tolerance of such compositions should be emphasized. The oligo- and polypeptides in soaps and personal care products thus produced are capable of promoting collagen formation in skin and hair and thus counteracting skin irritations.

According to a sixth aspect, the invention relates to a food product comprising the composition according to the invention.

According to a preferred embodiment, the total content of free amino acids, oligopeptides, and polypeptides in the food product is from 2 wt % to 25 wt %, preferably from about 5 to 10 wt %.

According to a preferred embodiment, the total quantity of free amino acids, oligopeptides, and polypeptides in the food product is 5 to 50 grams, preferably about 10 grams. This embodiment has the advantage that a significant percentage of the daily recommended protein dose can be covered by ingesting the food product. For adults ingesting about 50 to 100 grams of protein per day is recommended. With increased physical stress, the recommended amount of protein doubles.

According to a preferred embodiment, the food product is a beverage comprising magnesium and calcium. The ratio of magnesium to calcium in the beverage is preferably 1.25:1 to 3:1, more preferably about 2:1.

According to a preferred embodiment, the beverage is an ayran. The total amount of free amino acids, oligopeptides, polypeptides, and proteins without peptidases is preferably between 5 and 50 g per portion, more preferably about 10 g per portion. The ayran beverage preferably has exclusively vegetable amino acids, oligopeptides, and polypeptides, more preferably amino acids, oligopeptides, and polypeptides originating from soy protein. Preferably the beverage is essentially free of bacteria.

According to an alternative embodiment, the beverage comprises caffeine and/or taurine. Together with caffeine and/or taurine and in interaction with calcium and magnesium, the beverage according to the invention supplies the body with important nutrients and can thus improve the condition of early risers, night owls or nightshift workers, strengthen the body's defenses, and reduce the risk of infection due to overexertion.

According to a seventh aspect, the invention relates to a personal care product comprising the composition according to the invention.

According to a preferred embodiment, the personal care product is a therapeutic lotion or bath additive. The therapeutic lotion or bath additive is preferably a whey bath comprising enzymatically fermented whey.

The therapeutic lotion is preferably marketed as a ready-made product in a volume of 1 to 25 liters. The therapeutic lotion or bath additive preferably comprises neither soap nor shampoo. The therapeutic lotion or bath additive gently cleanses the skin and prevents it from drying out. It is capable of regenerating the acid mantle of the skin and helps heal skin inflammations and eczemas.

According to a preferred embodiment, the personal care product is a soap. The soap preferably has a pH of 5 to 7, more preferably about 5.5. This corresponds approximately to the pH of the skin and is therefore particularly gentle on the skin. However, soaps in the alkaline range, for example with a pH of about 7 to 8.5, are not excluded. It has been found that the peptides generated by enzymatic fermentation contained in the soap can reduce the negative effect of the soap on the acid mantle of the skin and enhance the regeneration of the skin. Soaps comprising the amino acid-containing composition produced by enzymatic fermentation can alleviate skin dryness and itching.

Also described herein are soaps comprising amino acids and peptides, which are obtained by enzymatic and/or bacterial fermentation.

EXAMPLES

Example 1

Whey protein concentrate WPC 80 with a dry matter content of 25% and a protein content of 80% in the dry matter was diluted 1:2 with water. The protein content of the solution thus produced was 10 wt %, based on the total weight of the solution produced.

The pH of this solution was adjusted to 5.5 with citric acid.

Two test preparations of 1 liter (100 g protein) each were produced. 2 g of an endopeptidase with an activity of about 1000 SAPU/g were added to each of the two preparations at the beginning and five more times in one-hour intervals. The total quantity of added endopeptidase was 12 g/100 g source protein in each case.

The preparations were incubated at 50° C.

After five hours, a 50 ml sample was taken from each preparation (samples I5 and II5—comparison example). The preparations were further incubated at 50° C. overnight.

The next morning, 2 g of an exopeptidase with about 900 CPGU were added to each of the two preparations five times in two-hour intervals. The total quantity of added exopeptidase was 10 g/100 g source protein in each case. The preparations were further incubated at 50° C.

Another 50 ml sample was then taken from each preparation (samples I9 and II9), and all four samples were analyzed.

To this end, the samples were homogenized. 0.5 g-2.5 g of the homogenized samples were weighed to the nearest 0.1 mg into a Falcon tube. 1 ml norleucine solution (0.1312 g/200 ml) were added as an internal standard (IS) and topped up to 25 ml with 3% 5-sulfosalicylic acid. The tubes were placed in a shaker and shaken vigorously for 20 minutes. They were then centrifuged at 5000 rpm for 5 minutes. The supernatant was filtered through a syringe filter (0.45 μm). 0.5 ml of the filtrate and 0.5 ml sample buffer for chromatography were pipetted into a reaction vessel, which was then sealed. The solution thus produced was used for chromatographic analysis on the amino acid analyzer.

In parallel, the amino acid composition of the fraction containing free amino acids and oligopeptides was determined. To this end, 0.5 g-2.5 g of the homogenized sample were again weighed to the nearest 0.1 mg into a Falcon tube. 2.5 ml norleucine solution (0.1312 g/200 ml) were pipetted in as an internal standard (IS) and topped up to 25 ml with 3% 5-sulfosalicylic acid. The tubes were shaken and centrifuged in the manner described above; the water-insoluble polypeptides and proteins contained in the precipitate were discarded. 1 ml of the supernatant was pipetted into a 50 ml glass digestion vessel, mixed with 9 ml 6N hydrochloric acid, and the vessels were tightly sealed with a screw cap. The vessels were placed in a heating block and the sample solution was digested for 8 h at 105° C. 2 ml of the digested solution were evaporated to dryness. The residue was taken up in 1 ml sample buffer for chromatography and transferred to a reaction vessel, which was then sealed. The solution thus produced was used for chromatographic analysis on the amino acid analyzer. In addition, the content of oligopeptides in the composition can be calculated by subtracting the content of free amino acids determined in step 1.

Table 1 shows the composition of the four samples that were analyzed.

TABLE 1

Sample composition

Results free amino acids:

| | Sample I 5 | Sample II 5 | Sample I 9 | Sample II 9 |
|---|---|---|---|---|
| | | mg/kg test preparation | | |
| essential amino acids (proteinogenic amino acids): | | | | |
| Threonine (Thr) | 57 | 56 | 709 | 738 |
| Valine (Val) | 112 | 111 | 977 | 949 |
| Methionine (Met) | 75 | 85 | 135 | 142 |
| Isoleucine (Iso) | 49 | 44 | 344 | 361 |
| Leucine (Leu) | 947 | 853 | >2800 | >2800 |
| Phenylalanine (Phe) | 175 | 143 | 843 | 815 |
| Lysine (Lys) | 1279 | 1209 | >2800 | >2800 |
| Tryptophan (Trp) | not determined | | | |
| semi-essential amino acids (proteinogenic amino acids): | | | | |
| Histidine (His) | 74 | 68 | 384 | 384 |
| Arginine (Arg) | 264 | 247 | 795 | 791 |
| non-essential amino acids (proteinogenic amino acids): | | | | |
| Aspartic acid (Asp) | 25 | 23 | 390 | 378 |
| Serine (Ser) | 60 | 57 | 395 | 404 |
| Asparagine (Asn) | 49 | 30 | 343 | 292 |
| Glutamic acid (Glu) | 308 | 248 | 1591 | 1588 |
| Glycine (Gly) | <10 | <10 | 116 | 124 |
| Alanine (Ala) | 105 | 93 | 634 | 665 |
| Cysteine (Cys) | not determined | | | |
| Tyrosine (Tyr) | 148 | 142 | 814 | 818 |
| Proline (Pro) | 29 | 40 | 104 | 125 |
| Glutamine (Gln) | not determined | | | |
| other determined substances | | | | |
| Taurine (Tau) | not analyzable | not analyzable | not analyzable | not analyzable |
| Citrulline (Cit) | <10 | <10 | 34 | 41 |
| Cystine (Cys2) | 186 | 189 | 341 | 348 |
| Cystathionine (Cystha) | 191 | 173 | not analyzable | not analyzable |
| 3-methyl-histidine (3Mehis) | <10 | <10 | <10 | <10 |
| 1-methyl-histidine (1Mehis) | <10 | <10 | <10 | <10 |
| Hydroxylysine (Hylys) | <10 | <10 | <10 | <10 |
| Ornithine (Orn) | <10 | <10 | <10 | <10 |
| Hydroxyproline (Hypro) | <10 | <10 | <10 | <10 |

Results NPN extract (oligopeptides and free amino acids:

| | Sample I 5 | Sample II 5 | Sample I 9 | Sample II 9 |
|---|---|---|---|---|
| | | mg/kg test preparation | | |
| essential amino acids (proteinogenic amino acids): | | | | |
| Threonine (Thr) | 4813 | 4641 | 5223 | 5266 |
| Valine (Val) | 2583 | 2672 | 3069 | 3287 |
| Methionine (Met) | 791 | 154 | 533 | 223 |
| Isoleucine (Iso) | 2968 | 2840 | 3410 | 3701 |
| Leucine (Leu) | 5909 | 5696 | 6864 | 6944 |
| Phenylalanine (Phe) | 1590 | 1564 | 1890 | 1846 |
| Lysine (Lys) | 5788 | 5490 | 6544 | 6530 |
| Tryptophan (Trp) | not determined | | | |
| semi-essential amino acids (proteinogenic amino acids): | | | | |
| Histidine (His) | 1081 | 1004 | 1239 | 1190 |
| Arginine (Arg) | 1300 | 1185 | 1360 | 1285 |

TABLE 1-continued

Sample composition non-essential amino acids (proteinogenic amino acids):

| | | | | |
|---|---|---|---|---|
| Aspartic acid (Asp) | 5459 | 5145 | not analyzable | 2004 |
| Serine (Ser) | 3344 | 2694 | 3394 | 3249 |
| Asparagine (Asn) | nn | nn | nn | nn |
| Glutamic acid (Glu) | 11235 | 9516 | 9333 | 8550 |
| Glycine (Gly) | 941 | 873 | 1038 | 975 |
| Alanine (Ala) | 3279 | 3123 | 3225 | 3176 |
| Cysteine (Cys) | not determined | | | |
| Tyrosine (Tyr) | 1122 | 860 | 1563 | 1420 |
| Proline (Pro) | 4722 | 4722 | 4644 | 4522 |
| Glutamine (Gln) | not determined | | | |
| other determined substances | | | | |
| Taurine (Tau) | not analyzable | not analyzable | not analyzable | not analyzable |
| Citrulline (Cit) | nn | nn | nn | nn |
| Cystine (Cys2) | 747 | 488 | 1374 | 1160 |
| Cystathionine (Cystha) | nn | nn | nn | nn |
| 3-methyl-histidine (3Mehis) | nn | nn | nn | nn |
| 1-methyl-histidine (1Mehis) | nn | nn | nn | nn |
| Hydroxylysine (Hylys) | nn | nn | nn | nn |
| Ornithine (Orn) | nn | nn | nn | nn |
| Hydroxyproline (Hypro) | nn | nn | nn | nn |

After hydrolysis was complete, about 50 to 60% oligopeptides and about 15% free amino acids, divided into about 10% essential amino acids and 5% non-essential amino acids, in each case based on the total weight of the source protein, in this case 100 g protein, were present in the preparations that were incubated with the endo- and exo-peptidases.

The pH, the lactose content, and taste of the four samples were also assayed. The results are summarized in Table 2.

TABLE 2

Taste analysis of the generated hydrolysates:

| | Sample I 5 | Sample II 5 | Sample I 9 | Sample II 9 | WPC 80 1:2 |
|---|---|---|---|---|---|
| pH | 4.97 | 5.03 | 5.04 | 5.10 | |
| Taste | not bitter | not bitter | not bitter | not bitter | |
| Lactose [g/100 g] | | | | 0.9 | 0.8 |

Example 2

Whey protein concentrate WPC 80 with a dry matter content of 25% and a protein content of 80% in the dry matter was diluted 1:2 with water. The protein content of the solution thus produced was 9.98 wt %, based on the total weight of the solution produced.

The pH of this solution was originally 6.32 and was then adjusted to 5.45 with citric acid.

The preparation volume was 2 liters in each case. An endopeptidase with an activity of about 1000 SAPU/g and an exopeptidase with about 900 CPGU were added. Enzymatic hydrolysis took place at 50° C.

Table 3 shows the hydrolysis scheme:

TABLE 3

Hydrolysis scheme

| Day | Time | Preparation EZ 40 | Preparation EZ 41 |
|---|---|---|---|
| Day 1 | 7:05 am | 2 g endopeptidase | 2 g endopeptidase |
|  | 9:05 am | 2 g endopeptidase | 2 g endopeptidase |
|  |  | 2 g exopeptidase | 2 g exopeptidase |
|  | 11:10 am | 2 g endopeptidase | 2 g endopeptidase |
|  |  | 2 g exopeptidase | 2 g exopeptidase |
|  | 2:10 pm | End | 4 g endopeptidase |
|  |  |  | 4 g exopeptidase |
| Day 2 | 9:00 am |  | End |
| Total quantity of endopeptidase [g/100 g source protein] |  | 3 g | 5 g |
| Total quantity of exopeptidase [g/100 g source protein] |  | 2 g | 4 g |

Samples were then taken and analyzed in the manner described in Example 1.

Table 4 shows the composition of the analyzed samples.

TABLE 4

Sample composition

| | Results free amino acids: | | Results NPN extract (oligopeptides and free amino acids: | |
|---|---|---|---|---|
| | EZ40 | EZ41 | EZ40 | EZ41 |
| | mg/kg test preparation | | | |
| essential amino acids (proteinogenic amino acids) | | | | |
| Threonine (Thr) | 143 | 434 | 3782 | 4482 |
| Valine (Val) | 166 | 513 | 2222 | 2694 |
| Methionine (Met) | 114 | 257 | 871 | 978 |
| Isoleucine (Iso) | 101 | 283 | 2458 | 2956 |
| Leucine (Leu) | 808 | <2000* | 4643 | >5500* |
| Phenylalanine (Phe) | 143 | 354 | 1217 | 1486 |
| Lysine (Lys) | 1147 | <2000* | <4000* | >4000* |
| Tryptophan (Trp) | not determined | | | |
| semi-essential amino acids (proteinogenic amino acids) | | | | |
| Histidine (His) | 124 | 253 | 727 | 949 |
| Arginine (Arg) | 256 | 536 | 956 | 1214 |
| non-essential amino acids (proteinogenic amino acids) | | | | |
| Aspartic acid (Asp) | 46 | 163 | 4136 | 5076 |
| Serine (Ser) | 125 | 289 | 2557 | 2957 |
| Asparagine (Asn) | 61 | 138 | <50 | <50 |
| Glutamic acid (Glu) | 261 | 666 | >8000* | >8000* |
| Glycine (Gly) | 19 | 48 | 685 | 878 |
| Alanine (Ala) | 124 | 381 | 2637 | >3000* |
| Cysteine (Cys) | not determined | | | |
| Tyrosine (Tyr) | 193 | 515 | 1064 | 1470 |
| Proline (Pro) | 21 | 79 | >4000* | >4000* |
| Glutamine (Gln) | not determined | | | |
| other determined substances | | | | |
| Taurine (Tau) | 68 | 83 | 87 | 90 |
| Citrulline (Cit) | <10 | <10 | <50 | <50 |
| Cystine (Cys2) | 103 | 261 | 399 | 516 |
| Cystathionine (Cystha) | <10 | <10 | <50 | <50 |
| 3-methyl-histidine (3Mehis) | <10 | <10 | <50 | <50 |
| 1-methyl-histidine (1Mehis) | <10 | <10 | <50 | <50 |
| Hydroxylysine (Hylys) | <10 | <10 | <50 | <50 |
| Ornithine (Orn) | <10 | <10 | <50 | <50 |
| Hydroxyproline (Hypro) | <10 | <10 | <50 | <50 |

The samples were also analyzed in terms of phase separation, pH, and taste. The results are summarized in Table 5.

TABLE 5

Taste analysis of the generated hydrolysates:

| | Sample EZ 40 | Sample EZ 41 |
|---|---|---|
| Phase separation | no | yes |
| pH | 4.50 | 4.47 |
| Taste | bitter | bitter |

Example 3

Whey protein concentrate WPC 80 with a dry matter content of 25% and a protein content of 80% in the dry matter was used diluted with water or undiluted.

Table 6 shows the composition of the test preparations with their pH values. A pH adjustment was not necessary.

TABLE 6

Composition of the test preparations

| | EZ 42 | EZ 43 | EZ 44 | EZ 45 |
|---|---|---|---|---|
| Protein content [%] | 11.27 | 20.43 | 11.27 | 10.00 |
| pH | 5.33 | 5.34 | 5.33 | 5.60 |
| Preparation volume [l] | 2 | 2 | 2 | 1 |

An endopeptidase with an activity of about 1000 SAPU/g and an exopeptidase with about 900 CPGU were added. Enzymatic hydrolysis took place at 50° C.

Table 7 shows the hydrolysis scheme.

TABLE 7

Hydrolysis scheme:

| Day | Time | EZ 42 | EZ 43 | EZ 44 |
|---|---|---|---|---|
| 1 | 10:00 am | 2 g endop. | 2 g endop. | 10 g endop. |
|  | 11:00 am | 2 g endop. | 2 g endop. |  |
|  | 12:00 noon | 2 g endop. | 2 g endop. |  |
|  | 1:00 pm | 2 g endop. | 2 g endop. |  |
|  | 2:00 pm | 2 g endop. | 2 g endop. |  |
|  | 4:00 pm | End of approach no. 1 | | |

TABLE 7-continued

Hydrolysis scheme:

| 2 | 7:00 am | End of approach no. 2 | | |
|---|---|---|---|---|
|   | 7:15 am | 2 g exop. | 2 g exop. | 8 g exop. |
|   | 8:15 am | 2 g exop | 2 g exop | |
|   | 9:15 am | 2 g exop | 2 g exop | |
|   | 10:15 am | 2 g exop. | 2 g exop | |
|   | 12:15 pm | End of approach no. 3 | | |

TABLE 7-continued

Hydrolysis scheme:

| Day | Time | EZ 45 |
|---|---|---|
| 1 | 7:15 am | 2.5 g endop. |
|   | 1:15 pm | End of approach no. 1 |
| 2 | 8:45 am | End of approach no. 2 |
|   | 7:30 am | 2 g exop. |
|   | 12:30 pm | End of approach no. 3 |

Samples were then taken and analyzed in the manner described in example 1.

Table 8 shows the composition of the analyzed samples.

TABLE 8

Sample composition

Results free amino acids:

| | EZ 42 | | | EZ 43 | | |
|---|---|---|---|---|---|---|
| | 6 h | 21 h | 26 h | 6 h | 21 h | 26 h |
| | | | mg/kg test preparation | | | |
| essential amino acids (proteinogenic amino acids) | | | | | | |
| Threonine (Thr) | 85 | 267 | 671 | 71 | 263 | 992 |
| Valine (Val) | 60 | 205 | 631 | 96 | 229 | 818 |
| Methionine (Met) | 150 | 341 | 453 | 203 | 415 | 632 |
| Isoleucine (Iso) | 39 | 156 | 398 | 70 | 186 | 465 |
| Leucine (Leu) | 522 | 1351 | 2536 | 582 | 1407 | 3049 |
| Phenylalanine (Phe) | 126 | 335 | 709 | 165 | 354 | 886 |
| Lysine (Lys) | 1102 | 1731 | 2898 | 1598 | 2126 | 3723 |
| Tryptophan (Trp) | not determined | | | not determined | | |
| semi-essential amino acids (proteinogenic amino acids) | | | | | | |
| Histidine (His) | 68 | 164 | 303 | 74 | 150 | 400 |
| Arginine (Arg) | 230 | 408 | 421 | 220 | 448 | 359 |
| non-essential amino acids (proteinogenic amino acids) | | | | | | |
| Aspartic acid (Asp) | 33 | 134 | 464 | 40 | 121 | 574 |
| Serine (Ser) | 69 | 169 | 368 | 70 | 170 | 613 |
| Asparagine (Asn) | nn | 164 | 386 | 39 | 99 | 609 |
| Glutamic acid (Glu) | 141 | 614 | 1909 | 194 | 553 | 2305 |
| Glycine (Gly) | 26 | 63 | 133 | 30 | 67 | 195 |
| Alanine (Ala) | 85 | 239 | 554 | 112 | 248 | 751 |
| Cysteine (Cys) | not determined | | | not determined | | |
| Tyrosine (Tyr) | 64 | 260 | 626 | 58 | 251 | 681 |
| Proline (Pro) | nn | 76 | 150 | nn | 72 | 236 |
| Glutamine (Glu) | not determined | | | not determined | | |
| other determined substances | | | | | | |
| Taurine (Tau) | not analyzable | not analyzable | not analyzable | not analyzable | not analyzable | not analyzable |
| Citrulline (Cit) | nn | nn | 156 | nn | nn | 431 |
| Cystine (Cys2) | nn | 62 | 156 | nn | nn | 431 |
| Cystathionine (Cystha) | 89 | 151 | 68 | 115 | 145 | 63 |
| 3-methyl-histidine (3Mehis) | nn | nn | nn | nn | nn | nn |
| 1-methyl-histidine (1Mehis) | nn | nn | nn | nn | nn | nn |
| Hydroxylysine (Hylys) | nn | nn | nn | nn | nn | nn |
| Ornithine (Orn) | nn | 19 | 55 | nn | nn | 96 |
| Hydroxyproline (Hypro) | nn | nn | nn | nn | nn | nn |
| Total | 2889 | 6909 | 14039 | 3755 | 7353 | 17935 |

TABLE 8-continued

Sample composition

Results NPN-extract
(oligopeptides and free amino acids):

| | EZ 42 | | | EZ 43 | | |
|---|---|---|---|---|---|---|
| | 6 h | 21 h | 26 h | 6 h | 21 h | 26 h |
| | | | mg/kg test preparation | | | | essential amino acids (proteinogenic amino acids)

| | | | | | | |
|---|---|---|---|---|---|---|
| Threonine (Thr) | 4151 | 5074 | 4963 | 5574 | 5355 | 1927 |
| Valine (Val) | 4016 | 3643 | 3687 | 5923 | 5821 | 5951 |
| Methionine (Met) | 423 | 768 | 755 | 1098 | 1073 | 307 |
| Isoleucine (Iso) | 3953 | 3864 | 4059 | 6293 | 6110 | 6356 |
| Leucine (Leu) | 8149 | 7809 | 7971 | 12565 | 12778 | 13637 |
| Phenylalanine (Phe) | 2316 | 2175 | 2261 | 3186 | 3285 | 3533 |
| Lysine (Lys) | 7261 | 6975 | 7228 | 10794 | 10943 | 12236 |
| Tryptophan (Trp) | | not determined | | | not determined | | semi-essential amino acids (proteinogenic amino acids)

| | | | | | | |
|---|---|---|---|---|---|---|
| Histidine (His) | 1536 | 1327 | 1544 | 2057 | 2103 | 2547 |
| Arginine (Arg) | 2308 | 1487 | 1321 | 2253 | 2599 | 1666 | non-essential amino acids (proteinogenic amino acids)

| | | | | | | |
|---|---|---|---|---|---|---|
| Aspartic acid (Asp) | 7188 | 6941 | 7287 | 10038 | 10948 | 10159 |
| Serine (Ser) | 2344 | 3104 | 3039 | 3161 | 2787 | 798 |
| Asparagine (Asn) | nn | nn | nn | nn | nn | nn |
| Glutamic acid (Glu) | 12268 | 12614 | 12217 | 15289 | 16814 | 7777 |
| Glycine (Gly) | 1763 | 1274 | 1386 | 1800 | 2119 | 2186 |
| Alanine (Ala) | 4958 | 4383 | 4159 | 7320 | 7204 | 7185 |
| Cysteine (Cys) | | not determined | | | not determined | |
| Tyrosine (Tyr) | 938 | 1316 | 1611 | 1522 | 1463 | 269 |
| Proline (Pro) | 5506 | 5271 | 4993 | 8859 | 8653 | 9694 |
| Glutamine (Glu) | | not determined | | | not determined | | other determined substances

| | | | | | | |
|---|---|---|---|---|---|---|
| Taurine (Tau) | not analyzable | not analyzable | not analyzable | not analyzable | not analyzable | not analyzable |
| Citrulline (Cit) | nn | nn | 130 | nn | nn | nn |
| Cystine (Cys2) | 1898 | 1175 | 1617 | 2515 | 3922 | 3235 |
| Cystathionine (Cystha) | nn | nn | nn | nn | nn | nn |
| 3-methyl-histidine (3Mehis) | nn | nn | nn | nn | nn | nn |
| 1-methyl-histidine (1Mehis) | nn | nn | nn | nn | nn | nn |
| Hydroxylysine (Hylys) | nn | nn | nn | nn | nn | nn |
| Ornithine (Orn) | nn | nn | 59 | nn | nn | 260 |
| Hydroxyproline (Hypro) | nn | nn | nn | nn | nn | nn |
| Total | 70976 | 69191 | 70287 | 100247 | 103977 | 89723 |

Results
free amino acids:

| | EZ 44 | | | EZ 45 | | |
|---|---|---|---|---|---|---|
| | 6 h | 21 h | 26 h | 6 h | 25.5 h | 30.5 h |
| | | | mg/kg test preparation | | | | essential amino acids (proteinogenic amino acids)

| | | | | | | |
|---|---|---|---|---|---|---|
| Threonine (Thr) | 76 | 463 | 695 | 35 | 385 | 517 |
| Valine (Val) | 49 | 417 | 612 | 11 | 364 | 471 |
| Methionine (Met) | 170 | 398 | 532 | 100 | 286 | 317 |
| Isoleucine (Iso) | 33 | 246 | 481 | 34 | 220 | 301 |
| Leucine (Leu) | 576 | 1798 | 2731 | 237 | 1142 | 1592 |
| Phenylalanine (Phe) | 146 | 498 | 757 | 93 | 347 | 479 |
| Lysine (Lys) | 1141 | 2192 | 2961 | 691 | 1350 | 1831 |
| Tryptophan (Trp) | | not determined | | | not determined | | semi-essential amino acids (proteinogenic amino acids)

| | | | | | | |
|---|---|---|---|---|---|---|
| Histidine (His) | 76 | 208 | 330 | 36 | 128 | 209 |
| Arginine (Arg) | 219 | 462 | 406 | 126 | 340 | 394 |

TABLE 8-continued

| Sample composition | | | | | | |
|---|---|---|---|---|---|---|
| non-essential amino acids (proteinogenic amino acids) | | | | | | |
| Aspartic acid (Asp) | 48 | 251 | 232 | 28 | 93 | 156 |
| Serine (Ser) | 61 | 257 | 384 | 39 | 219 | 278 |
| Asparagine (Asn) | nn | 220 | 356 | nn | 146 | 154 |
| Glutamic acid (Glu) | 156 | 1070 | 2099 | 118 | 924 | 1382 |
| Glycine (Gly) | 10 | 94 | 152 | nn | 63 | 101 |
| Alanine (Ala) | 93 | 369 | 606 | 66 | 291 | 431 |
| Cysteine (Cys) | not determined | | | not determined | | |
| Tyrosine (Tyr) | 80 | 382 | 684 | 27 | 250 | 412 |
| Proline (Pro) | nn | 94 | 173 | nn | nn | 194 |
| Glutamine (Glu) | not determined | | | not determined | | |
| other determined substances | | | | | | |
| Taurine (Tau) | not analyzable | not analyzable | not analyzable | not analyzable | not analyzable | not analyzable |
| Citrulline (Cit) | nn | 58 | 105 | nn | nn | 58 |
| Cystine (Cys2) | 27 | 59 | 228 | nn | 23 | 55 |
| Cystathionine (Cystha) | 48 | 89 | 136 | 31 | 48 | nn |
| 3-methyl-histidine (3Mehis) | nn | nn | nn | nn | nn | nn |
| 1-methyl-histidine (1Mehis) | nn | nn | nn | nn | nn | nn |
| Hydroxylysine (Hylys) | nn | nn | nn | nn | nn | nn |
| Ornithine (Orn) | nn | 13 | 146 | nn | 29 | 54 |
| Hydroxyproline (Hypro) | nn | nn | nn | nn | nn | 51 |
| Total | 3009 | 9638 | 14806 | 1672 | 6648 | 9437 |

| Results NPN-extract (oligopeptides and free amino acids): | | | | | | |
|---|---|---|---|---|---|---|
| | EZ 44 | | | EZ 45 | | |
| | 6 h | 21 h | 26 h | 6 h | 25.5 h | 30.5 h |
| | mg/kg test preparation | | | | | |
| essential amino acids (proteinogenic amino acids) | | | | | | |
| Threonine (Thr) | 5627 | 2394 | 6272 | 2782 | 4669 | 3677 |
| Valine (Val) | 3457 | 3624 | 3881 | 3236 | 3310 | 3361 |
| Methionine (Met) | 950 | 455 | 1300 | 444 | 714 | 510 |
| Isoleucine (Iso) | 3503 | 3849 | 4129 | 3443 | 3566 | 3598 |
| Leucine (Leu) | 7474 | 7984 | 8521 | 6684 | 6916 | 7196 |
| Phenylalanine (Phe) | 2091 | 1891 | 2503 | 1721 | 1955 | 1994 |
| Lysine (Lys) | 6759 | 7179 | 7806 | 5881 | 5975 | 6121 |
| Tryptophan (Trp) | not determined | | | not determined | | |
| semi-essential amino acids (proteinogenic amino acids) | | | | | | |
| Histidine (His) | 1247 | 1419 | 1695 | 1115 | 1229 | 1327 |
| Arginine (Arg) | 1567 | 1349 | 1336 | 1264 | 1444 | 1332 |
| non-essential amino acids (proteinogenic amino acids) | | | | | | |
| Aspartic acid (Asp) | 6711 | 6333 | 8226 | 5793 | 6098 | 6405 |
| Serine (Ser) | 3763 | 1070 | 4374 | 1523 | 2960 | 2174 |
| Asparagine (Asn) | nn | nn | nn | nn | nn | nn |
| Glutamic acid (Glu) | 13549 | 10107 | 14520 | 10546 | 11651 | 10480 |
| Glycine (Gly) | 1163 | 1324 | 1571 | 1010 | 1114 | 1208 |
| Alanine (Ala) | 4496 | 4273 | 4609 | 4061 | 3880 | 3918 |
| Cysteine (Cys) | not determined | | | not determined | | |
| Tyrosine (Tyr) | 1379 | 545 | 1995 | 546 | 1322 | 1086 |
| Proline (Pro) | 5490 | 5579 | 5819 | 5146 | 5035 | 4910 |
| Glutamine (Glu) | not determined | | | not determined | | |
| other determined substances | | | | | | |
| Taurine (Tau) | not analyzable | not analyzable | not analyzable | not analyzable | not analyzable | not analyzable |
| Citrulline (Cit) | nn | nn | nn | nn | nn | nn |
| Cystine (Cys2) | 742 | 1765 | 1276 | 1207 | 1059 | 1583 |
| Cystathionine (Cystha) | 48 | 89 | 136 | 31 | 48 | nn |
| 3-methyl-histidine (3Mehis) | nn | nn | nn | nn | nn | nn |
| 1-methyl-histidine (1Mehis) | nn | nn | nn | nn | nn | nn |

TABLE 8-continued

| | Sample composition | | | | | |
|---|---|---|---|---|---|---|
| Hydroxylysine (Hylys) | nn | nn | nn | nn | nn | nn |
| Ornithine (Orn) | nn | nn | 139 | nn | nn | 64 |
| Hydroxyproline (Hypro) | nn | nn | nn | nn | nn | nn |
| Total | 69968 | 61140 | 79972 | 56402 | 62897 | 60944 |

The samples were analyzed specifically in terms of their taste. The samples were not bitter.

What is claimed is:

1. A process for producing a composition comprising free amino acids, oligopeptides, and polypeptides, comprising:
   adding at least one purified microbial exopeptidase and at least one purified microbial endopeptidase to a composition comprising at least one protein; and
   incubating the at least one exopeptidase, the at least one endopeptidase and the composition at a temperature of 40° C.-60° C.;
   wherein:
   prior to adding the at least one purified microbial exopeptidase and at least one purified microbial endopeptidase, the concentration of the at least one protein in the composition is 5-30 wt % based on the total weight of the composition;
   prior to adding the at least one purified microbial exopeptidase and at least one purified microbial endopeptidase, the pH of the composition is 4-6; and
   the amount of the at least one purified microbial exopeptidase and at least one purified microbial endopeptidase added to the composition is 2-10 grams of each peptidase per 100 grams of the at least one protein.

2. The process according to claim 1, wherein the microbial origin of the at least one exopeptidase and the at least one endopeptidase is bacterial or fungal.

3. The process according to claim 1, wherein prior to adding at least one exopeptidase and the at least one endopeptidase, the concentration of the at least one protein in the composition is 10-20 wt % based on the total weight of the composition.

4. The process according to claim 1, wherein the incubating occurs 1-24 hours.

5. The process according to claim 1, wherein the incubating temperature is 45° C.-60° C.

6. The process according to claim 1, wherein, prior to adding the at least one exopeptidase and the at least one endopeptidase, the pH of the composition is 4.5-6.

7. The process according to claim 1, further comprising adding calcium carbonate and/or magnesium carbonate.

8. The process according to claim 1, wherein the at least one protein in the composition is selected from the group consisting of whey, a whey protein concentrate, a milk protein concentrate, a slurry from food production, a distillery slurry, a brewery slurry, pea, lentil, bean, soybean, and combinations of two or more thereof.

9. The process according to claim 1, wherein the amount of each of the at least one exopeptidase and the at least one endopeptidase added is 500-20,000 U per 100 grams of the at least one protein in the composition.

10. The process according to claim 1, wherein at least one of the at least one purified microbial exopeptidase and the at least one purified microbial endopeptidase is added repeatedly to the composition.

11. The process according to claim 10, wherein the at least one of the at least one exopeptidase and the at least one endopeptidase is repeatedly added in equal amounts and at equal time intervals.

12. The process according to claim 1, wherein the at least one endopeptidase is added prior to adding the at least one exopeptidase.

13. The process according to claim 1, wherein the composition is first incubated with the at least one endopeptidase for 1-10 hours, and then incubated with the at least one exopeptidase for 3-40.

14. The process according to claim 13, wherein the at least one endopeptidase and/or the at least one exopeptidase is/are added in equal amounts at equal time intervals.

15. A composition produced by the process according to claim 1, comprising free amino acids, oligopeptides, and polypeptides, wherein:
   0.5-25 wt % of the composition is free amino acids, based on a total weight of free amino acids, oligopeptides, polypeptides, and proteins without the added peptidases; and
   25-65 wt % of the composition is oligopeptides, excluding the wt % of the at least one exopeptidase and the at least one endopeptidase.

16. The composition according to claim 15, wherein the composition comprises from 0.3-13 wt % of the free amino acids and the free amino acids are selected from the group consisting of isoleucine, lysine, methionine, phenylalanine, threonine, tryptophan, valine, and combinations thereof.

17. The composition according to claim 15, wherein 0-40 wt % of the at least one protein is present as uncleaved protein.

18. The composition according to claim 15, wherein the composition has a pH of 3-7.

19. The composition according to claim 15, further comprising magnesium and calcium in a weight ratio of 1.25:1-3:1 magnesium:calcium.

20. A food product comprising the composition according to claim 15, wherein the food product is selected from the group consisting of a fruit juice beverage, a milk beverage, a whey beverage, a yogurt, an ayran, and a kefir.

21. A personal care product comprising the composition according to claim 15, wherein the care product is a soap, a shampoo, a hair treatment, a hair mask, a hair pack, a hair tonic, a conditioner, a bath essence, a body lotion, a body gel, a lotion for treating rosacea, a cream for treating acne, a facial mask or a facial cream.

22. The food product according to claim 20, wherein a total content of the free amino acids, the oligopeptides, and the polypeptides is from 2 wt % to 25 wt % of the food product.

23. The food product according to claim 20, wherein a total content of the free amino acids, the oligopeptides, and the polypeptides in the food product is from 5 to 50 grams.

* * * * *